US005695758A

United States Patent [19]

Bosslet et al.

[11] Patent Number: 5,695,758
[45] Date of Patent: *Dec. 9, 1997

[54] MONOCLONAL ANTIBODIES AGAINST TUMOR-ASSOCIATED ANTIGENS, PROCESSES FOR THE PREPARATION THEREOF AND THE USE THEREOF

[75] Inventors: Klaus Bosslet; Peter Pfleiderer, both of Marburg; Gerhard Seemann, Marburg-Elnhausen, all of Germany

[73] Assignee: Behringwerke Aktiengesellschaft, Marburg, Germany

[*] Notice: The term of this patent shall not extend beyond the expiration date of Pat. No. 5,639,621.

[21] Appl. No.: 478,857

[22] Filed: Jun. 7, 1995

Related U.S. Application Data

[63] Continuation of Ser. No. 957,827, Oct. 8, 1992, abandoned.

[30] Foreign Application Priority Data

Oct. 11, 1991 [DE] Germany .................. 41 33 791.3

[51] Int. Cl.$^6$ .................. A61K 39/395; C12N 5/12
[52] U.S. Cl. .................. 424/133.1; 424/138.1; 424/174.1; 435/328; 435/330; 435/344; 435/355; 530/387.3; 530/387.7; 530/388.8
[58] Field of Search .................. 424/133.1, 137.1, 424/138.1, 139.1, 155.1, 174.1, 184.1, 185.1, 277.1; 435/69.6, 70.21, 172.2, 172.3, 174.1, 328, 330, 344, 355; 530/300, 350, 387.7, 388.8, 388.85, 389.7, 387.3

[56] References Cited

FOREIGN PATENT DOCUMENTS

| 0 141 079 | 5/1985 | European Pat. Off. . |
|---|---|---|
| 0 239 400 | 9/1987 | European Pat. Off. . |
| 0256654A2 | 2/1988 | European Pat. Off. . |
| 0376746A2 | 7/1990 | European Pat. Off. . |
| 0388914A1 | 9/1990 | European Pat. Off. . |
| 0397419A2 | 11/1990 | European Pat. Off. . |
| 0420394A1 | 4/1991 | European Pat. Off. . |
| 0443599A2 | 8/1991 | European Pat. Off. . |
| 38 25 615 | 2/1990 | Germany . |

OTHER PUBLICATIONS

"Monoclonal Antibodies Identify a CEA Crossreacting Antigen of 95 kD (NCA–95) Distinct in Antigenicity and Tissue Distribution From the Previously Described NCA of 55 kD", Buchegger et al., Int. J. Cancer, 33:643–649 (1984).
"Quantitative considerations supporting the irrelevance of circulating serum CEA for the immunoscintigraphic visualization of CEA expressing carcinomas", Bosslet et al., Eur. J. Nucl. Med., 14:523–528 (1988).
"Isolation and Characterization of Mucin–Like Glycoprotein in Human Milk Fat Globule Membrane", Shimizu et al., J. Biochem, 91:515–524 (1982).
"A Core Protein Epitope of the Polymorphic Epithelial Mucin Detected by the Monoclonal Antibody SM–3 is Selectively Exposed in a Range of Primary Carcinomas", Girling et al., Int. J. Cancer, 43:1072–1076 (1989).

"Monoclonal Antibodies to Epithelium–Specific Components of the Human Milk Fat Gloubule Membrane: Production and Reaction With Cells in Culture", Taylor–Papadimitriou et al., Int. J. Cancer, 28:17–21 (1981).
"A Decade of Development in Immunoassay Methodology", Gosling, Clin. Chem., 36(8): 1408–1427 (1990).
"Immunoenzymatic Labeling of Monoclonal Antibodies Using Immune Complexes of Alkaline Phosphatase and Monoclonal Anti–alkaline Phosphatase (APAAP Complexes)", Cordell et al., Journal of Histochemistry and Cytochemistry, 32(2): 219–229 (1984).
"Cloning immunoglobulin variable domains for expression by the polymerase chain reaction", Orlandi et al., Proc.Natl.Acad.Sci.USA,86:3833–3837(1989).
"DNA sequencing with chain–terminating inhibitors", Sanger et al., Proc. Natl.Acad.Sci. USA, 74(12): 5463–5467 (1977).
"Monoclonal Antibody Therapeutic Trials in Seven Patients With T–Cell Lymphoma", Miller et al., Blood, 62(5): 988–995 (1983).
"In vivo labelling of granulocytes with $^{99m}$Tc anti–NCA monoclonal anti-bodies for imaging inflammation", Joesph et al., Eur.J.Nucl.Med., 14:367–373 (1988).
"Replacing the complementarity–determining regions in a human antibody with those from a mouse", Jones et al., Nature, 321:522–525 (1986).
"Reshaping human antibodies for therapy", Riechmann et al., Nature, 332:323–327 (1988).
"Reshaping Human Antibodies: Grafting an Antilysozyme Activity", Verhoeyen et al., Science, 239:1534–1536 (1988).
"Sequence of Proteins of Immunological Interest", Kabat et al.,4th Edition, US Department of Health and Human Services, US Government Printing Office (1987).
"Molecular Cloning, A Laboratory Manual", Sambrook, Fritsch, Maniatis; Cold Spring Harbor Laboratory, pp. 11–44,51–127,133–134,141,146,150–167, 170, 188–193, 197–199, 248–255, 270–294, 310–328, 364–401, 438–506, (1982).
"Molecular Cloning, A Laboratory Manual", Sambrook, Fritsch, Maniatis; Second Edition, Cold Spring Harbor Press, pp. 16.20–16, 16.30–16.40, 16.54–16.55, (1989).
"Isolation of overproducing recombinant mammalian cell lines by a fast and simple selection procedure", Wirth et al., Gene 73: 419–426 (1988).
"Evolution of Human Immunoglobulin k J Region Genes*", Hieter et al., The Journal of Biological Chemistry, 257(3): 1516–1522 (1982).

(List continued on next page.)

Primary Examiner—Lila Feisee
Assistant Examiner—Julie E. Reeves
Attorney, Agent, or Firm—Finnegan, Henderson, Farabow, Garrett & Dunner, L.L.P.

[57] ABSTRACT

The invention relates to monoclonal antibodies against a tumor-associated antigen which is mainly derived from tumors from the group of carcinomas of the breast, ovaries and prostate, as well as adenocarcinomas of the lung, which additionally react with polymorphic epithelial mucin (PEM), to the preparation and use thereof and to the use of the epitope defined by the antibody for diagnosis and therapy.

6 Claims, 17 Drawing Sheets

OTHER PUBLICATIONS

"Humanization of Monoclonal Antibodies", Güssow et al., Methods in Enzymology, 203:99–121 (1991).

"Design and Synthesis of a Mimetic from an Antibody Complementarity-Determining Region", Saragovi et al., Science, 253:792–795 (1991).

"The immobilization of immunoreactants on solid phases", Tijssen, Practice & Theory of Enzyme Immunoassays, pp. 297–328, (1984).

"Differential Reactivity of a Novel Monoclonal Antibody (DF3) with Human Malignant versus Benign Breast Tumors", Kufe et al., Hybridoma, 3(3): 223–232 (1984).

Price et al Cancer Immunol Immunother. 1990 vol. 31 : 269–272.

Girling, et al.; International Journal of Cancer, vol. 43, pp. 1072–1076; 1989.

Jones, et al.; Nature, vol. 321, pp. 522–525; May 29, 1986.

Güssow, et al.. ; Methods in Enzymology, vol. 203, pp. 99–121; 1991.

Burchell, et al.; Cancer Research, vol. 47, pp. 5476–5482; Oct. 15, 1987.

Briggs et al. 1993 Euro J. Cancer vol. 29A(2): 230–237.

Paul et al 1993 Fundamental Immunology p. 242.

```
          10                    30                    50
     L  Q  S  L  R  A  L  V  Q  P  G  G  S  M  K  L  S  C  V  A
     CTGCAGAGTCTGAGAGCCTTGGTGCAACCTGGAGGATCCATGAAACTCTCCTGTGTTGCC 70                    90                   110
     S  G  F  T  F  S  N  Y  W  M  N  W  V  R  Q  S  P  E  K  G
     TCTGGATTCACTTTCAGTAACTACTGGATGAACTGGGTCCGCCAGTCTCCAGAGAAGGGG 130                   150                   170
     L  E  W  V  A  E  I  R  L  K  S  N  N  Y  A  T  H  Y  A  E
     CTTGAGTGGGTTGCTGAAATTAGATTGAAATCTAATAATTATGCAACACATTATGCGGAG 190                   210                   230
     S  V  K  G  R  F  T  I  S  R  D  D  S  K  S  S  V  Y  L  Q
     TCTGTGAAAGGGAGGTTCACCATCTCAAGAGATGATTCCAAAAGTAGTGTCTACCTGCAA 250                   270                   290
     M  N  N  L  R  A  E  D  T  G  I  Y  Y  C  I  R  E  T  V  F
     ATGAACAACTTAAGAGCTGAAGACACTGGCATTTATTACTGTATCAGGGAGACGGTTTTT 310                   330
     Y  Y  Y  A  M  D  Y  W  G  Q  G  T  T  V  T
     TATTACTATGCTATGGACTACTGGGGCCAAGGGACCACGGTCACC
```

```
        10                    30                    50
Q   L   T   Q   S   P   P   S   V   P   V   T   P   G   E   S   V   S   I   S
CAGCTGACCCAGTCTCCACCCTCTGTACCTGTCACTCCTGGAGAGTCAGTATCCATCTCC 70                    90                   110
C   R   S   S   Q   S   L   L   H   G   D   G   N   T   Y   L   Y   W   F   L
TGCAGGTCTAGTCAGAGTCTCCTGCATGGTGATGGCAACACTTACTTGTATTGGTTCCTG 130                   150                   170
Q   R   P   G   Q   S   P   R   L   L   I   Y   R   M   S   N   L   A   S   G
CAGAGGCCAGGCCAGTCTCCTCGGCTCCTGATATATCGGATGTCCAACCTTGCCTCAGGA 190                   210                   230
V   P   D   R   F   S   G   S   G   S   G   T   A   F   T   L   R   I   S   R
GTCCCAGACAGGTTCAGTGGCAGTGGGTCAGGAACTGCTTTCACACTGAGAATCAGTAGA 250                   270                   290
V   E   A   E   D   V   G   V   Y   Y   C   M   Q   H   L   E   Y   P   F   T
GTGGAGGCTGAGGATGTGGGTGTTTATTACTGTATGCAACATCTAGAATATCCTTTCACG

310
F   G   G   G   K   V   E   I
TTCGGAGGGGGCAAGGTGGAGATCA
```

FIG. 6
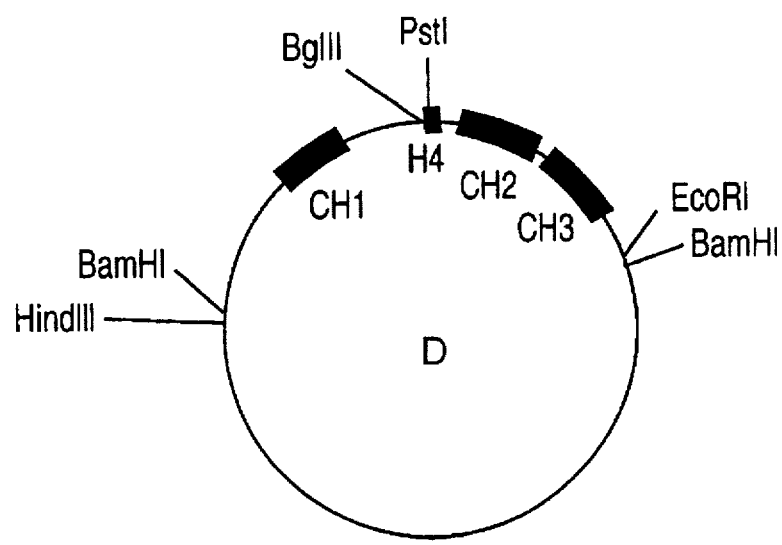
Bam HI PARTIAL
FILL IN
T4 LIGASE
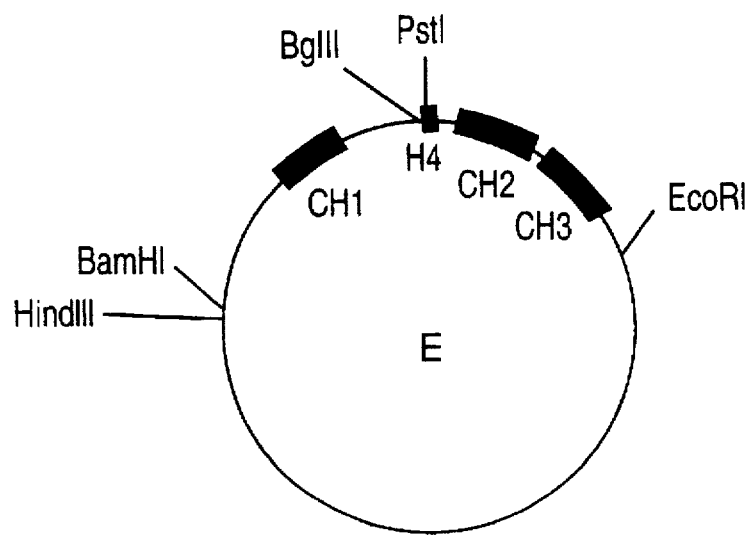

FIG. 10
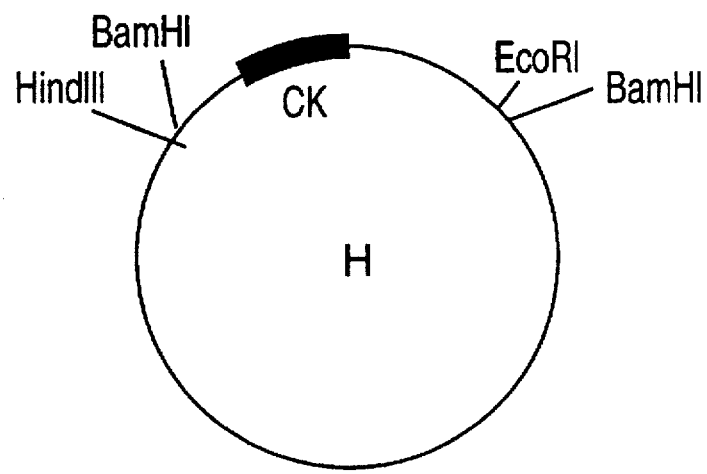
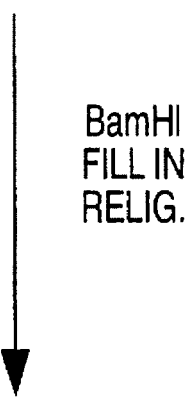
BamHI
FILL IN
RELIG.
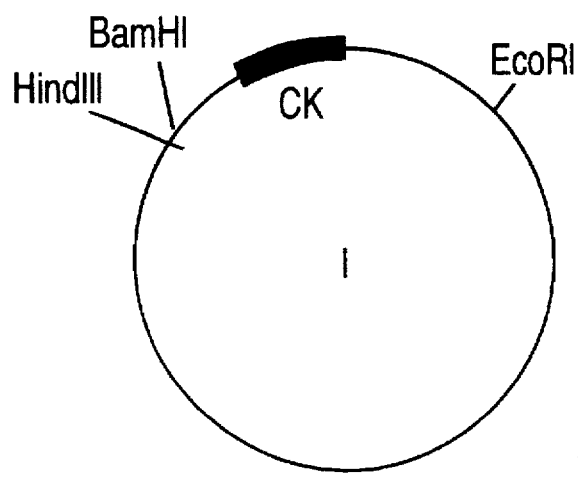

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 115 amino acids
        ( B ) TYPE: amino acid ( D ) TOPOLOGY: linear ( i i ) MOLECULE TYPE: peptide ( x i ) SEQUENCE DESCRIPTION: SEQ ID NO:1:

```
Leu Gln Ser Leu Arg Ala Leu Val Gln Pro Gly Gly Ser Met Lys Leu
1               5                   10                  15

Ser Cys Val Ala Ser Gly Phe Thr Phe Ser Asn Tyr Trp Met Asn Trp
            20                  25                  30

Val Arg Gln Ser Pro Glu Lys Gly Leu Glu Trp Val Ala Glu Ile Arg
        35                  40                  45

Leu Lys Ser Asn Asn Tyr Ala Thr His Tyr Ala Glu Ser Val Lys Gly
    50                  55                  60

Arg Phe Thr Ile Ser Arg Asp Asp Ser Lys Ser Ser Val Tyr Leu Gln
65                  70                  75                  80

Met Asn Asn Leu Arg Ala Glu Asp Thr Gly Ile Tyr Tyr Cys Ile Arg
                85                  90                  95

Glu Thr Val Phe Tyr Tyr Tyr Ala Met Asp Tyr Trp Gly Gln Gly Thr
            100                 105                 110

Thr Val Thr
    115
```

( 2 ) INFORMATION FOR SEQ ID NO:2:

( i ) SEQUENCE CHARACTERISTICS:
( A ) LENGTH: 345 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

```
CTGCAGAGTC TGAGAGCCTT GGTGCAACCT GGAGGATCCA TGAAACTCTC CTGTGTTGCC     60
TCTGGATTCA CTTTCAGTAA CTACTGGATG AACTGGGTCC GCCAGTCTCC AGAGAAGGGG   120
CTTGAGTGGG TTGCTGAAAT TAGATTGAAA TCTAATAATT ATGCAACACA TTATGCGGAG   180
TCTGTGAAAG GGAGGTTCAC CATCTCAAGA GATGATTCCA AAAGTAGTGT CTACCTGCAA   240
ATGAACAACT TAAGAGCTGA AGACACTGGC ATTTATTACT GTATCAGGGA GACGGTTTTT   300
TATTACTATG CTATGGACTA CTGGGGCCAA GGGACCACGG TCACC                  345
```

( 2 ) INFORMATION FOR SEQ ID NO:3:

( i ) SEQUENCE CHARACTERISTICS:
( A ) LENGTH: 108 amino acids
( B ) TYPE: amino acid
( D ) TOPOLOGY: linear ( i i ) MOLECULE TYPE: peptide ( x i ) SEQUENCE DESCRIPTION: SEQ ID NO:3:

```
Gln Leu Thr Gln Ser Pro Pro Ser Val Pro Val Thr Pro Gly Glu Ser
1               5                   10                  15

Val Ser Ile Ser Cys Arg Ser Ser Gln Ser Leu Leu His Gly Asp Gly
            20                  25                  30

Asn Thr Tyr Leu Tyr Trp Phe Leu Gln Arg Pro Gly Gln Ser Pro Arg
        35                  40                  45

Leu Leu Ile Tyr Arg Met Ser Asn Leu Ala Ser Gly Val Pro Asp Arg
    50                  55                  60

Phe Ser Gly Ser Gly Ser Gly Thr Ala Phe Thr Leu Arg Ile Ser Arg
```

```
     65                  70                  75                  80

Val Glu Ala Glu Asp Val Gly Val Tyr Tyr Cys Met Gln His Leu Glu
                85                  90                  95

Tyr Pro Phe Thr Phe Gly Gly Gly Lys Val Glu Ile
            100                 105
```

( 2 ) INFORMATION FOR SEQ ID NO:4:

( i ) SEQUENCE CHARACTERISTICS:
        ( A ) LENGTH: 325 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CAGCTGACCC  AGTCTCCACC  CTCTGTACCT  GTCACTCCTG  GAGAGTCAGT  ATCCATCTCC     60

TGCAGGTCTA  GTCAGAGTCT  CCTGCATGGT  GATGGCAACA  CTTACTTGTA  TTGGTTCCTG    120

CAGAGGCCAG  GCCAGTCTCC  TCGGCTCCTG  ATATATCGGA  TGTCCAACCT  TGCCTCAGGA    180

GTCCCAGACA  GGTTCAGTGG  CAGTGGGTCA  GGAACTGCTT  TCACACTGAG  AATCAGTAGA    240

GTGGAGGCTG  AGGATGTGGG  TGTTTATTAC  TGTATGCAAC  ATCTAGAATA  TCCTTTCACG    300

TTCGGAGGGG  GCAAGGTGGA  GATCA                                            325
```

MONOCLONAL ANTIBODIES AGAINST TUMOR-ASSOCIATED ANTIGENS, PROCESSES FOR THE PREPARATION THEREOF AND THE USE THEREOF

This application is a continuation, of application Ser. No. 07/957,827, filed Oct. 8, 1992, now abandoned.

The invention relates to monoclonal antibodies against a tumor-associated antigen which is mainly derived from tumors from the group of carcinomas of the breast, ovaries and prostate, as well as adenocarcinomas of the lung, which additionally react with polymorphic epithelial mucin (PEM), to the preparation and use thereof and to the use of the epitope defined by the antibody for diagnosis and therapy.

Hybridoma technology has made it possible to prepare specific monoclonal antibodies (MAbs) even against unpurified antigens. This fact has made it possible to identify a large number of tumor-associated antigens (TAAs) which occur on certain human tumors but also on normal human tissues. Examples of such TAAs are CEA (carcinoembryonic antigen), N-CAM (neural cell adhesion molecule) and PEM (polymorphic epithelial mucin).

CEA is mainly expressed on adenocarcinomas of the gastro-intestinal tract, N-CAM is located on tumors derived from neuroectoderm, and PEM occurs mainly on carcinomas of the breast and ovaries. The TAAs which have just been mentioned are high molecular weight glycoproteins which carry a large number of immunogenic epitopes for the murine immune system. Comparative immunohistochemical investigations on cryopreserved human tissues demonstrate that the specificity of an MAb which recognizes with its idiotype (V region) an epitope I on a TAA may show a different tissue binding than an MAb which recognizes an epitope II (Buchegger et al. (1984), Int. J. Cancer 33: 643–649).

Multifarious reasons are possible for this observation: crypticity of epitopes in certain tissues, cross-reactive epitopes on different antigens, changes in conformation of antigens on secretion from tissues into the plasma (Bosslet et al. (1988), Eur. J. Nucl. Med. 14: 523–528) etc. It may be concluded from this that the specificity of an MAb is not unambiguously given by the definition of the recognized antigen but is given by the exact description of the V region of the MAb in conjunction with its immunohistochemical specificity for cryopreserved human tissues and its serum specificity with circulating TAA structures in human serum or plasma.

Thus, for example, a number of MAbs against the PEM which was isolated by Shimizu from human milk, (Shimizu, M. and Yamauchi, K. (1982), J. Biochem. 91, 515–524) have been developed and bind to different epitopes and, accordingly, have different properties (Girling et al. (1989), 43, 1072–1076, Taylor-Papadimitriou et al. (1981), Int. J. Cancer, 28, 17–21).

Certain anti-PEM MAbs (HMFG 1,2) show a strong reaction with human carcinomas of the breast and ovaries but also react significantly with normal human tissues (Taylor-Papadimitriou et al. (1981)). Other MAbs (SM 3, Girling et al. (1989)) react more weakly and heterogeneously with carcinomas of the breast and ovaries but, on the other hand, do not bind significantly to normal human tissue.

We have succeeded, surprisingly, in producing an anti-PEM MAb which reacts strongly with carcinomas of the breast, ovaries and prostate, as well as adenocarcinomas of the lung, binds only weakly to normal human tissue and, in addition, is able to detect PEM very specifically in human serum or plasma. Methods for the immunochemical determination of antigen are known to the person skilled in the art (see Gosling (1990), Clin. Chem. 36/8, 1408–1427). In this connection a distinction is made essentially between two classes: homogeneous assays such as, for example, particle-enhanced nephelometry or turbidimetry and heterogeneous methods, also called solid-phase assays.

Solid-phase assays are designed so that the analyte antigen is immobilized out of the sample to be investigated by a trapping antibody bound to a solid phase, and the immobilized antigen is detected by a second antibody provided with a detectable labeling moiety (conjugate). Detectable labels of this type are known to the person skilled in the art, and examples are enzymes, chemiluminescent or electrochemiluminescent, radioactive or else colored labels.

The hybridoma cell line BW 835 which produces the monoclonal antibody BW 835 was deposited on Oct. 11, 1991, at DSM, Deutsche Sammlung von Mikroorganismen und Zellkulturen GmbH, Mascheroder Weg 1b, D-3300 Braunschweig, under the number DSM ACC2022.

Antibodies within the meaning of this invention also mean antibody fragments.

BRIEF DESCRIPTION OF THE DRAWINGS

FIG. 1a is the nucleic acid sequence of BW 835 $V_H$.

FIG. 1b is the nucleic acid sequence of BW 835 $V_K$.

FIG. 6 shows the cloning of plasmid D to obtain plasmid E. See Example 5.

FIG. 10 shows the partial cleavage of clone H to obtain plasmid I. See Example 9.

Figure 2:
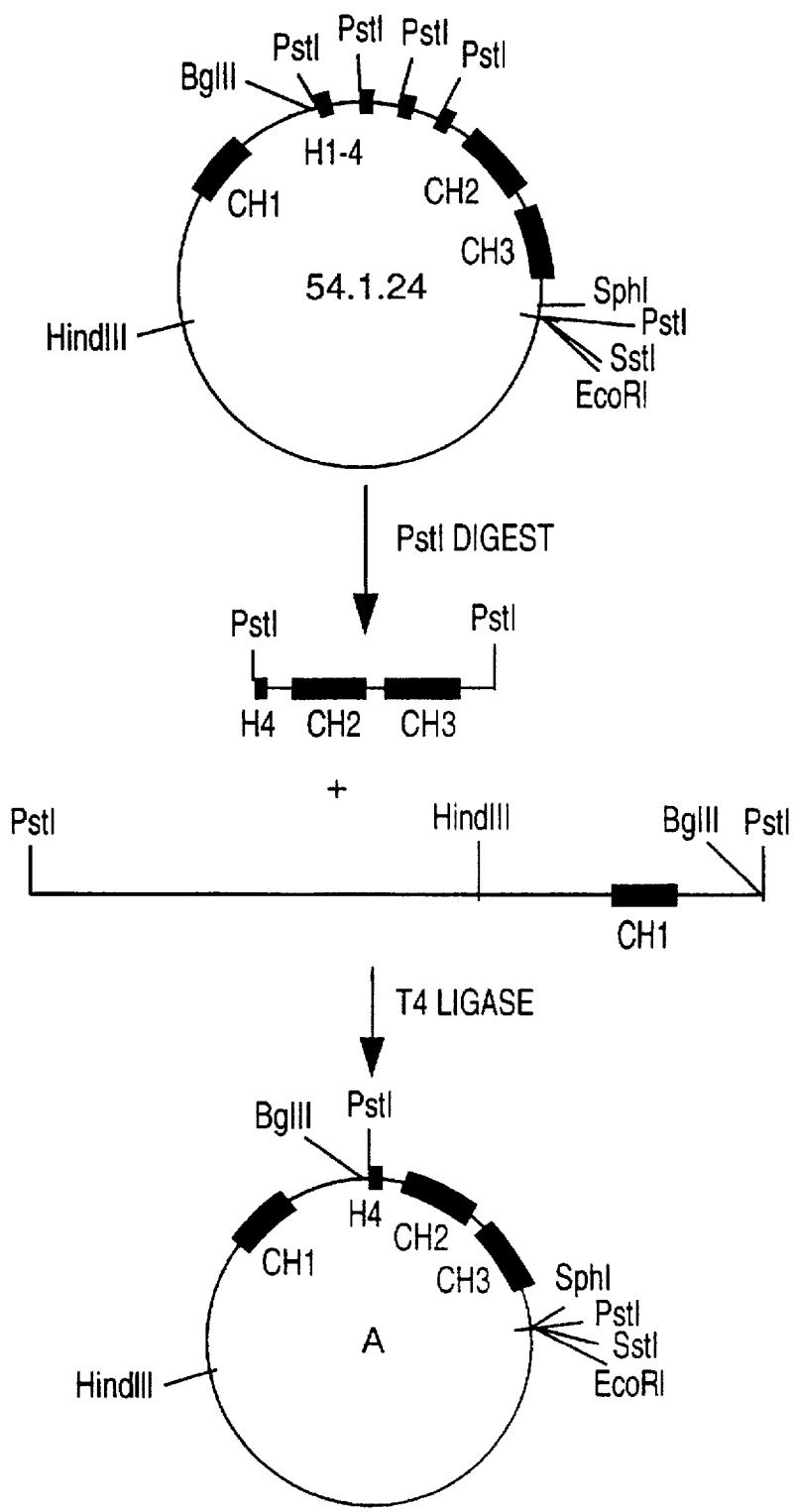
FIG. 2 shows the cloning of plasmid A which harbors a human $IgG_3\Delta C$ gene in which the H1, H2, and H3 exons have been deleted. See Example 1.

The preparation and the properties of this MAb (BW 835) are described below:

The MAb was generated by immunizing Balb/c mice with the MCF-7 and SW-613 breast carcinoma cell lines by methods known from the literature (EP-A2-0 141079).

The distribution of the epitope defined by the MAb BW 835 on cryopreserved human carcinomas and normal human tissues is shown in Tables Ia and b respectively, comparing with the MAb SM-3 (Girling et al. 1989). The data are based on an immunohistochemical detection with the APAAP technique (Cordell at al. (1984), J. Histochem. Cytochem. 32, 219). It can clearly be seen that MAb BW 835 reacts strongly with all 15 carcinomas of the breast from 15 tested carcinomas of the breast, whereas the MAb SM-3 detects only 11 of 15 carcinomas of the breast.

In the case of carcinoma of the ovaries, the MAb BW 835 reacts strongly with 6 of 8 tested tumors, and the MAb SM-3 reacts with a few cells in 6 of 8 carcinomas. With all the other carcinoma types tested, especially the adenocarcinomas of the lung and the carcinomas of the prostate, MAb BW 835 shows a quantitatively stronger reaction. These data show that MAb BW 835 detects more carcinomas with a quantitatively stronger reaction than the MAb SM-3 disclosed in the literature.

The binding of MAb BW 835 to normal human tissue is shown in Table Ib. The APAAP technique was employed to obtain the data in this case too. The epitope defined by MAb BW 835 is expressed significantly on the ductal epithelium of the breast and the ductal epithelium of the pancreas, and is weakly expressed on the surface epithelium of the lungs, on some nerve fibers and on the collecting tubules and the glomeruli of the kidney. All the other tested normal tissues are negative.

Because of its high selectivity, the MAb BW 835 can also be used as inducer for internal image anti-paratope MAbs. MAbs of this type might be employed as epitope vaccine for the therapy of human tumors.

The demonstration that the epitope defined by the MAb BW 835 is located on the PEM defined by MAb SM-3 was checked by a double-determinant assay.

TABLE Ib

Binding of the MAb BW 835 to cryopreserved normal human tissue

Tissue type:

Mammary gland

Positive reaction with the acinar epithelium, positive apical staining of the epithelium in the ducts and in some secreting vesicles Ovary Negative Pancreas Positive apical staining in the ducts Liver Negative Spleen Negative Colon Negative Stomach Negative Mucosa and some mucin-containing ducts with positive reaction Lung Surface epithelium of the lung with weak positive reaction Kidney Some glomeruli weakly stained, positive apical staining of the collecting tubules Brain Negative Peripheral nerve Some nerve fibers weakly stained Bone marrow Negative Peripheral blood components Lymphocytes, monocytes, granulocytes, erythrocytes, platelets are negative The MAb BW 835 used as trap was able to trap from cell culture supernatants of the T47 cell line an antigen which was detectable by the enzyme-labeled MAb SM-3. Furthermore, in the Western blot both MAbs stain molecules which correspond to the molecular weight position of PEM.

TABLE Ia

Binding of the MAb BW 835 to cryopreserved human tumors

| | | | | | | | | Lung carcinomas | | |
|---|---|---|---|---|---|---|---|---|---|---|
| | | | | Human tumor type | | | | | | |
| MAb | Carcinomas of the breast pos./total | Ovarian carcinomas pos./total | Prostate carcinomas pos./total | Stomach carcinomas pos./total | Colon carcinomas pos./total | Pancreas carcinomas pos./total | SCLC pos./ total | adeno pos./total | Squamous cell pos./total | Large cell pos./total |
| BW 835 | 15/15 | 6/8 | 4°/5 | 4*/6 | 3*/4 | 4*/7 | 4*/10 | 11°/12 | 5*/11 | 7°/11 |
| SM 3 | 11/15 | 6*/8 | 1°/5 | 3*/6 | 1°/4 | 3°/7 | 2*/10 | 6*/12 | 4*/11 | 3*/11 |

*a few cells positive
°a few areas of secreted products positive

Once the immunological specificity data for the MAb BW 835 were defined, the mRNA was isolated from $10^8$ hybridoma cells which secrete the MAb BW 835, the V genes of the heavy and light chains of the MAb BW 835 were isolated by the method described by Orlandi et al. (1989), Proc. Natl. Acad. Sci. USA: 86, 3833–3837, and the nucleic acid sequence of the essential regions of the V gene exons were determined by the method described by Sanger et al. (1977), Proc. Natl. Acad. Sci., USA: 74, 5463–5467 (FIGS. 1a, b) (SEQ ID NOS: 1-4).

On repeated high-dose administration of MAbs of murine origin, such as, for example, the MAb BW 835, for in vivo therapy of humans it is possible to immunize the patients. They are able to produce human anti-mouse immunoglobulin antibodies (HAMA) after about 10–14 days (Miller et al., (1983), Blood, 62, 988; Joseph et al., (1988), European Journal of Nuclear Medicine, 14, 367). These HAMAs may have unfavorable effects on the pharmacokinetics and pharmacodynamics of the MAb and impede continuation of the treatment.

In order to reduce the immunogenicity of xenogenic antibodies as far as possible, a technique in which only the CDR loops of the $V_L$ and $V_H$ domains of the xenogenic antibodies are transferred to $V_L$ and $V_H$ domains of human antibodies has been developed (Jones, P. T., et al., (1986), Nature, 321, 522) (EP-A-87302620, G. Winter), and this process is called "humanization" and takes place at the level of the $V_H$ and $V_L$ genes.

The technical procedure for humanization of an antibody is divided essentially into three sections: the cloning and nucleic acid sequence analysis of the specific $V_H$ and $V_L$ genes, the computer-assisted design of the synthetic oligonucleotides for the transfer of the CDR loops to the human $V_H$ and $V_L$ domains and the transfer of the CDR loops to human $V_H$ and $V_L$ domains by specific mutagenesis (Rieckmann, L., et al., (1988), Nature, 332, 323; Verhoeyen, M., et al., (1988), Science, 239, 1534).

Humanization of this type can also be carried out on MAb BW 835 in order to improve its usability in vivo. This would entail the authentic CDR regions of the BW 835 $V_H$ and $V_L$ domains (defined by Kabat, E. A., et al. (1987) Sequences of Proteins of Immunological Interest, fourth edition, US Dept. of Health and Human Services, US Government Printing Office) or CDR regions with a few modified amino acids being transferred to human $V_H$ and $V_L$ domains, it being possible for a few amino acids of the framework regions located between the CDR regions to be taken over from the mouse antibody to the humanized antibody in order to minimise the change in the antigen-binding properties of the resulting MAb BW 835 in the humanized form.

The variable domains of the humMAb BW 835 are accordingly composed of the framework regions, which are authentic or modified at a few points, of the variable domains of a human MAb onto which the CDR regions which are authentic or have been modified at a few aminoacid positions of the mouse MAb BW 835 have been transplanted.

The following examples describe the steps necessary for cloning and nucleic acid sequence analysis of the V genes and for the expression of BW 835 specificity as chimeric MAb. The techniques used in Examples 1–12 were, unless otherwise indicated, taken from Molecular Cloning, a Laboratory Manual; Sambrook, Fritsch, Maniatis; Cold Spring Harbor Laboratory, 1982 (pages 11–44, 51–127, 133–134, 141, 146, 150–167, 170, 188–193, 197–199, 248–255, 270–294, 310–328, 364–401, 437–506) and from Molecular Cloning, A Laboratory Manual, Second Edition; Sambrook, Fritsch, Maniatis; Cold Spring Harbor Laboratory Press, 1989 (pages 16.2–16.22, 16.30–16.40, 16.54–16.55).

EXAMPLE 1

The plasmid clone 54.1.24 which harbors the human $IgG_3\Delta C$ gene (FIG. 2) (DE-A1-38 25 615, FIG. 2) was cleaved with PstI. The vector resulting from this was ligated to the largest of the resulting PstI insert fragments and transformed into bacteria. The plasmid clone A which harbors a human $IgG_3\Delta C$ gene in which the H1, H2 and H3 exons have been deleted (IgG3Δ) was identified by restriction analysis and nucleic acid sequence determination.

EXAMPLE 2

Figure 3:
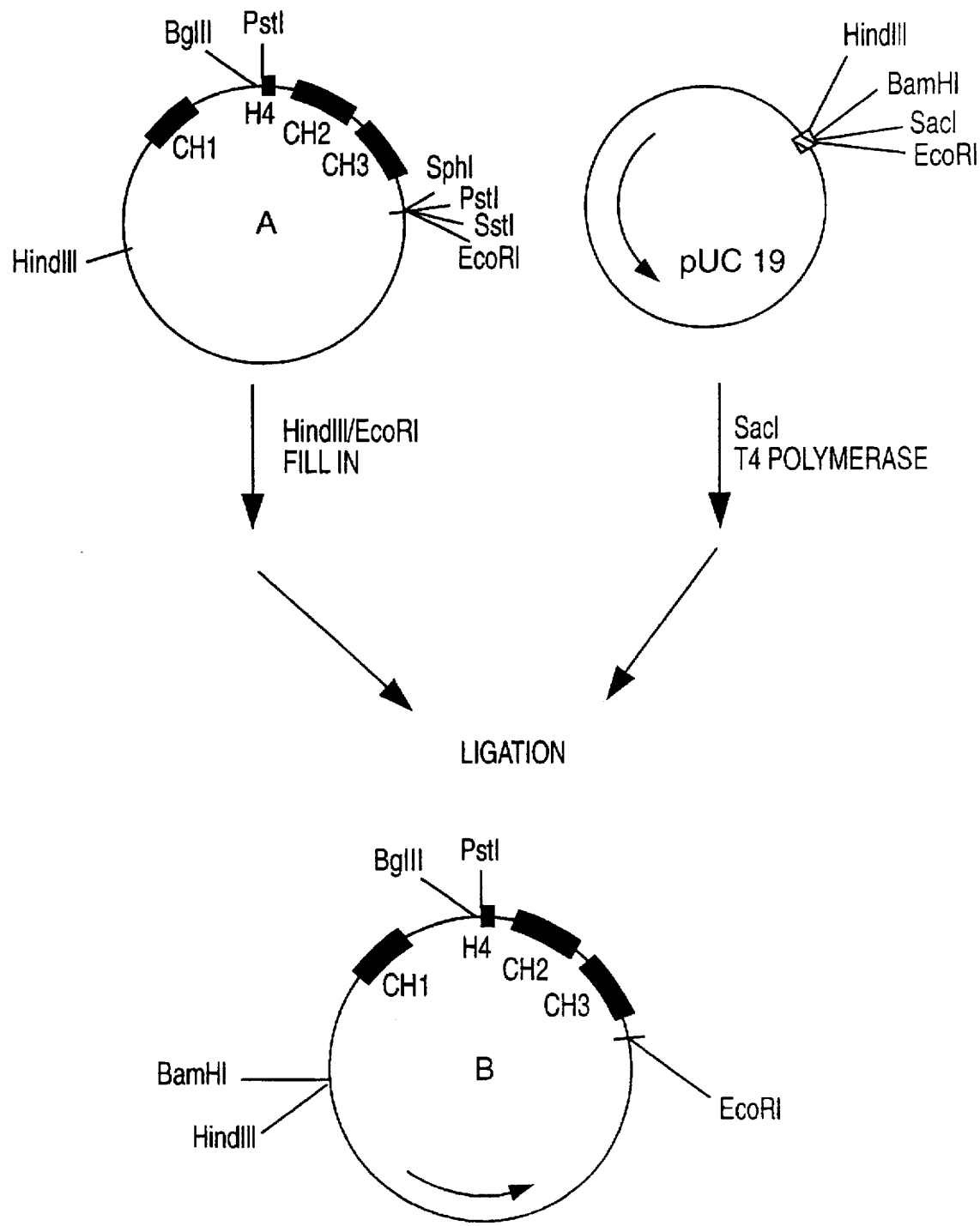
FIG. 3 shows the cloning of plasmid B. See Example 2.

The plasmid clone A was cleaved with HindIII and EcoRI, the ends were filled in with Klenow polymerase, the $IgG_3\Delta$ insert was isolated and ligated into a pUC19 vector cleaved with SstI and provided with blunt ends with the aid of $T_4$ polymerase. A plasmid clone B in which the $IgG_3\Delta$ gene is orientated so that the HindIII cleavage site is located at the 5' end and the EcoRI cleavage site is located at the 3' end of the pUC19 polylinker was identified by restriction mapping and nucleic acid sequence analysis (FIG. 3).

EXAMPLE 3

Figure 4:
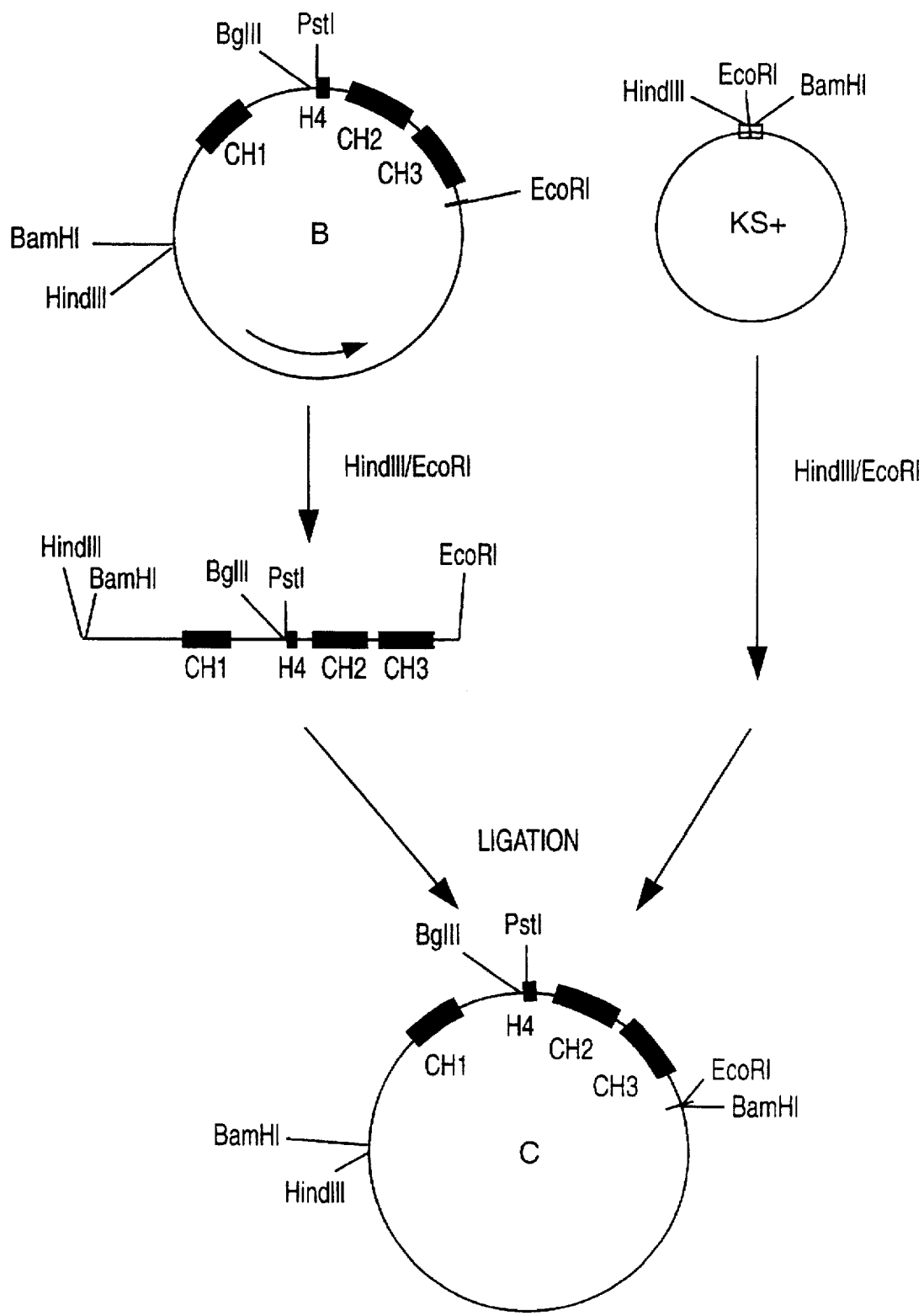
FIG. 4 shows the cloning of plasmid C. See Example 3.

The plasmid clone B was cleaved with EcoRI and HindIII, the $IgG_3\Delta$ insert was isolated and ligated into a KS+ plasmid vector (pBluescriptII KS+; Stratagene, La Jolla, Calif.) likewise cleaved with HindIII and EcoRI. The plasmid clone C in which the $IgG_3\Delta$ gene is flanked at the 5' and at the 3' end by a BamHI cleavage site was isolated (FIG. 4).

EXAMPLE 4

Figure 5:
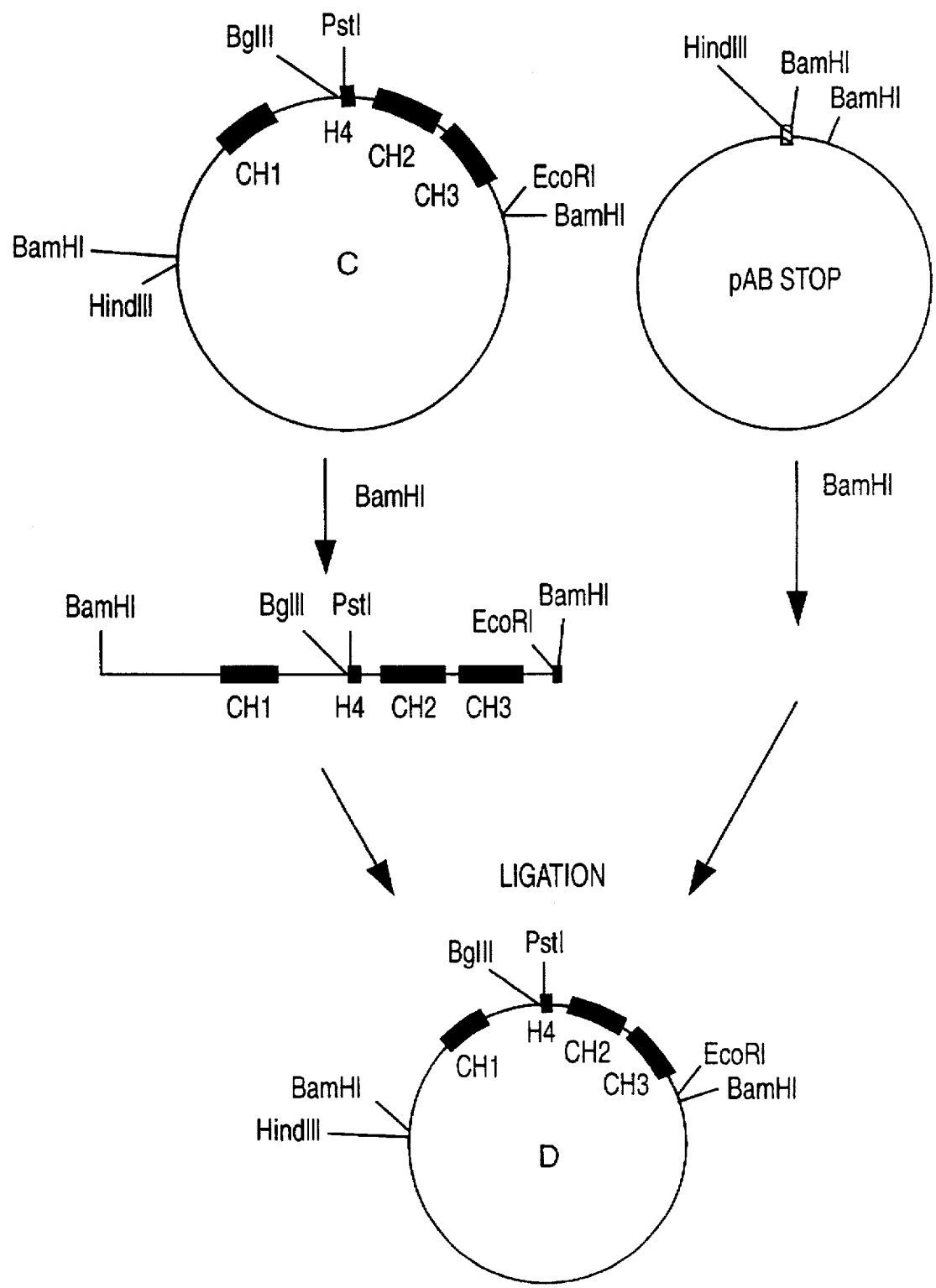
FIG. 5 shows the cloning of plasmid D. See Example 4.

The plasmid clone C was cleaved with BamHI, the $IgG_3\Delta$ insert was isolated and ligated into the expression vector pABStop (Wirth et al. (1988), Gene, 73, 419–426) likewise cleaved with BamHI. The expression plasmid D which contains the $IgG_3\Delta$ C gene in the orientation shown in FIG. 5 was identified. In this cloning the pABStop vector loses the polyadenylation signal and SV40 stop located between the two BamHI cleavage sites.

EXAMPLE 5

The expression plasmid D was partially cleaved with BamHI, the ends were filled in with Klenow polymerase and religated. The expression plasmid E in which the BamHI cleavage site 3' from the $IgG_3\Delta$ gene is destroyed was isolated (FIG. 6).

EXAMPLE 6

Figure 7:
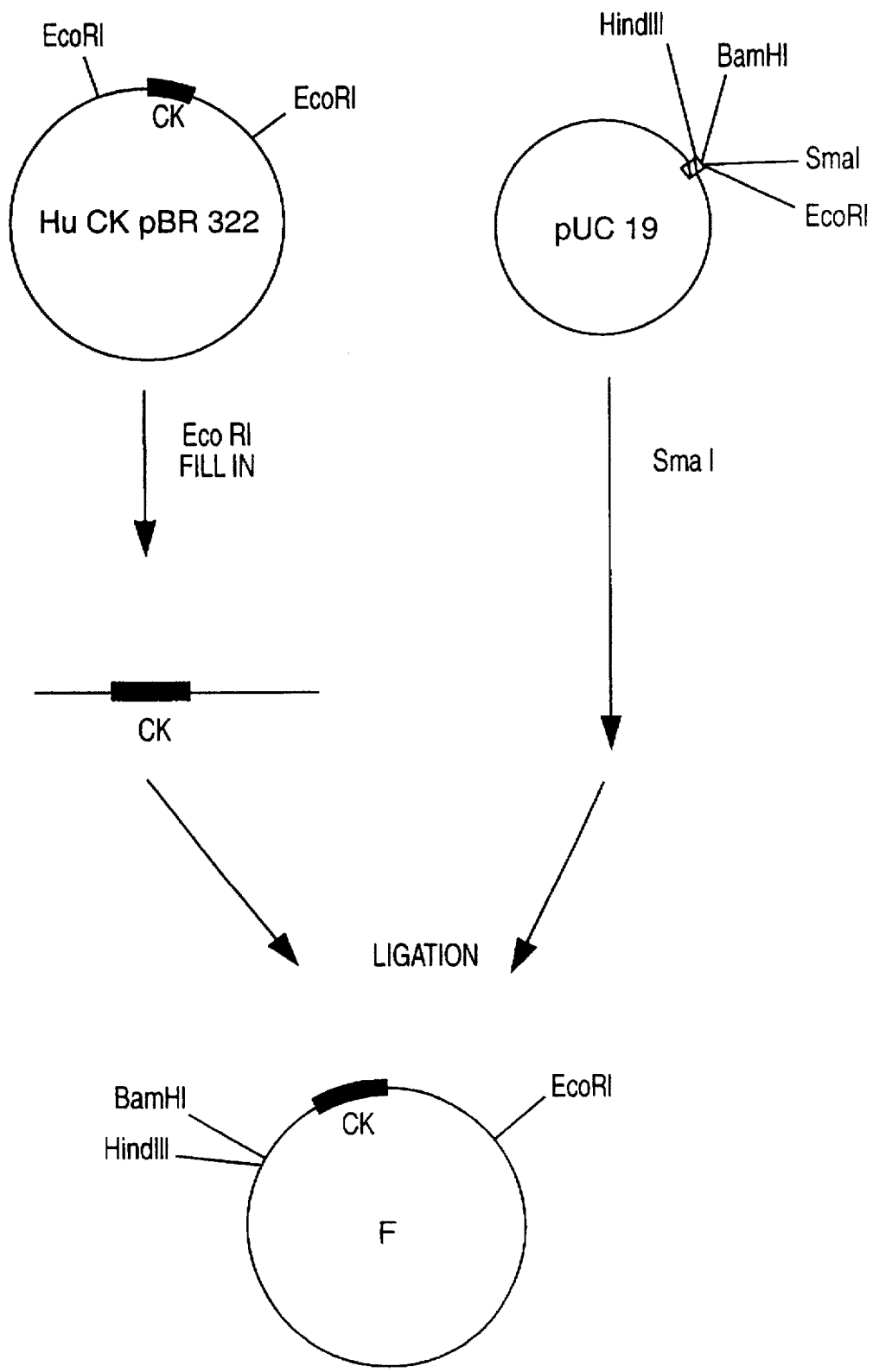
FIG. 7 shows the isolation of plasmid F. See Example 6.

The human C kappa gene (Hieter et al. (1982), J. Biol. Chem., 257, No. 3, 1516–1522) was obtained as EcoRI fragment cloned in pBR 322 from Prof. P. Leder, Harvard Medical School. The pBR322 vector was cleaved with EcoRI, the EcoRI cleavage sites were filled in, the C kappa insert was isolated and ligated into a pUC19 vector cleaved with SmaI. The plasmid clone F in which the C kappa gene is flanked at the 5' end by a HindIII after a BamHI cleavage site and at the 3' end by an EcoRI cleavage site was isolated (FIG. 7).

EXAMPLE 7

The plasmid clone F was cleaved with HindIII and EcoRI, the C kappa insert was isolated and cloned into a HindIII/

Figure 8:
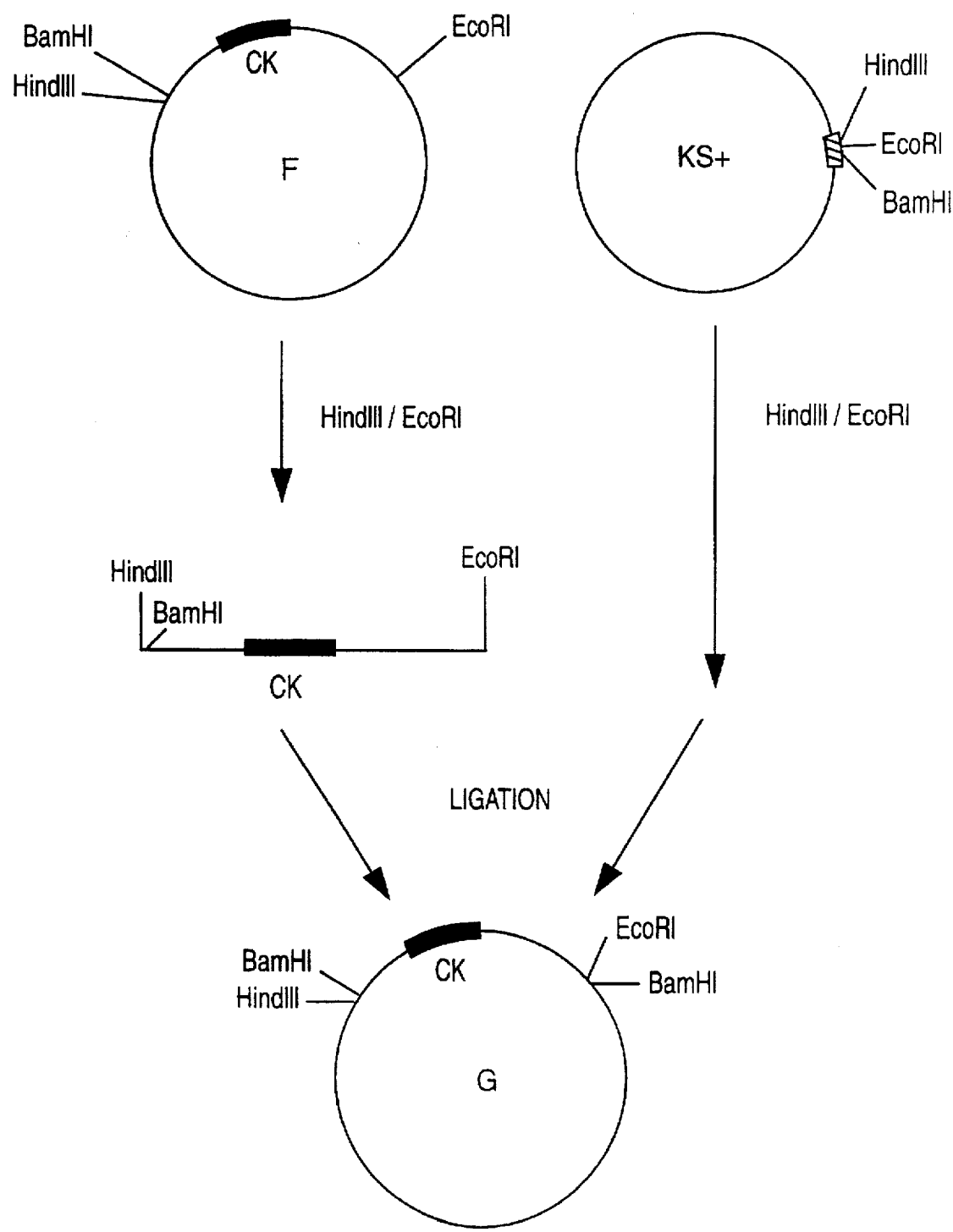
FIG. 8 shows the cleavage of plasmid F to obtain plasmid G. See Example 7.

EcoRI-cleaved KS+ plasmid. The plasmid clone G in which the C kappa insert is flanked at the 5' and at the 3' end by a BamHI cleavage site was isolated (FIG. 8).

EXAMPLE 8

Figure 9:
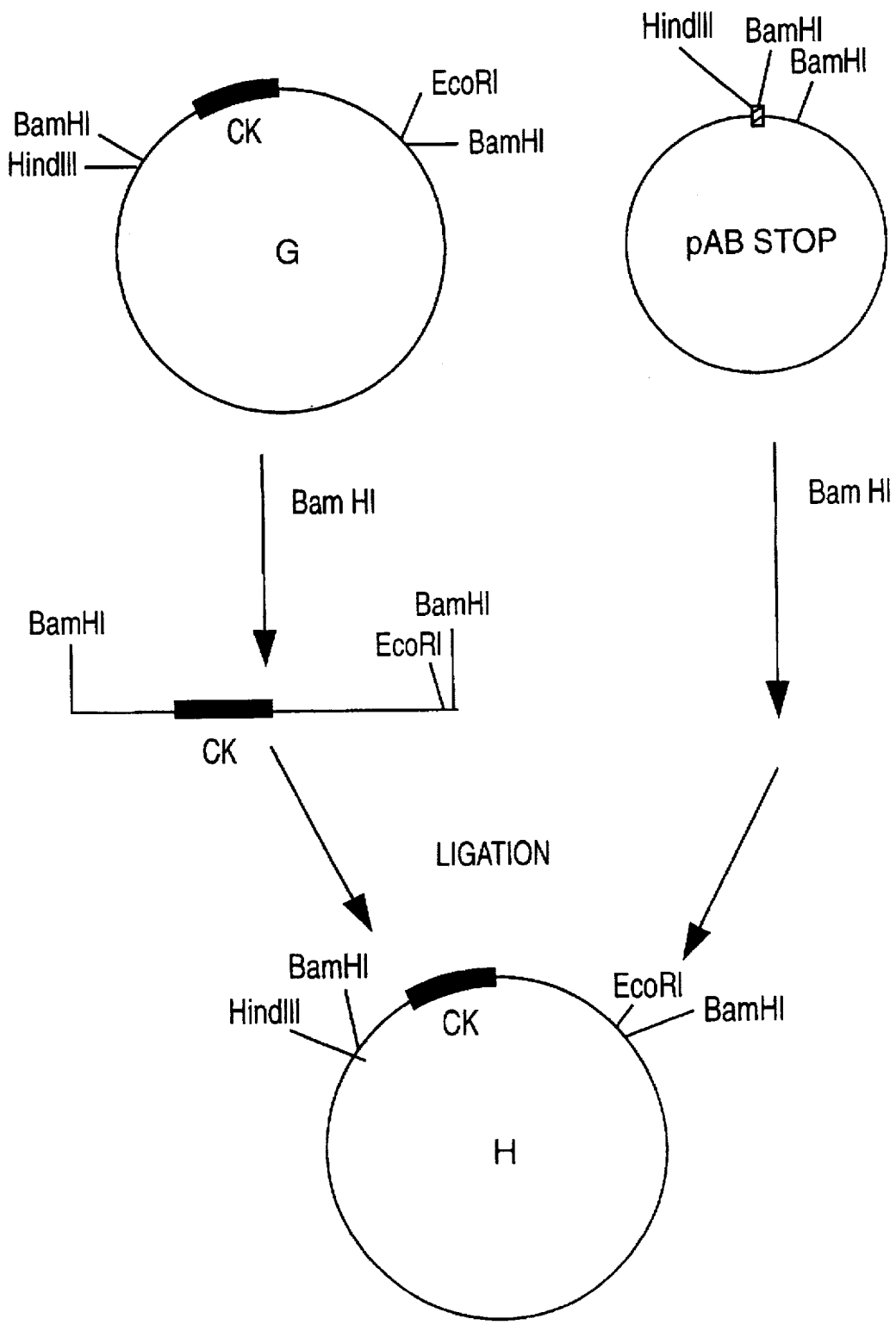
FIG. 9 shows the cleavage of plasmid E to obtain plasmid H. See Example 8.

The plasmid clone G was cleaved with BamHI, the C kappa insert was isolated and cloned into a pAB stop vector cleaved with BamHI. The clone H in which the C kappa gene is orientated so that the HindIII cleavage site of the pAB stop vector is located at its 5' end was identified by restriction mapping and nucleic acid sequence analysis (FIG. 9).

EXAMPLE 9

The clone H was partially cleaved with BamHI, the restriction ends were filled in and religated. The clone I in which the BamHI cleavage site 3' of the C kappa gene is destroyed was identified by restriction mapping (FIG. 10).

EXAMPLE 10

Figure 11A:
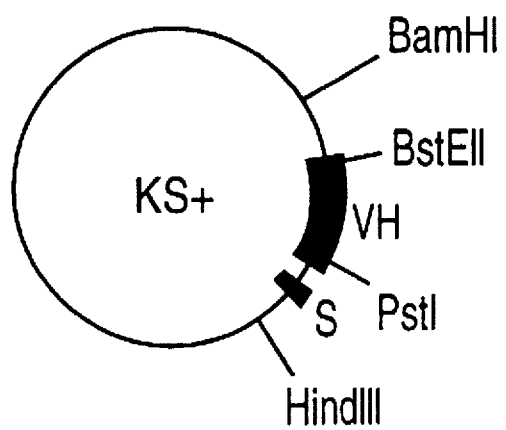
FIG. 11a shows the restriction cleavage sites for MAb BW 835 $V_H$. See Example 12.
Figure 11B:
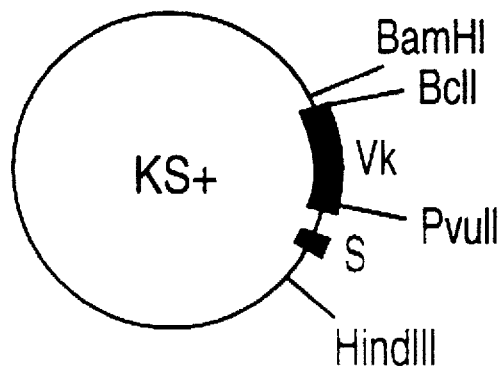
FIG. 11b shows the restriction cleavage sites for MAb BW 835 $V_K$. See Example 12.
Figure 12:
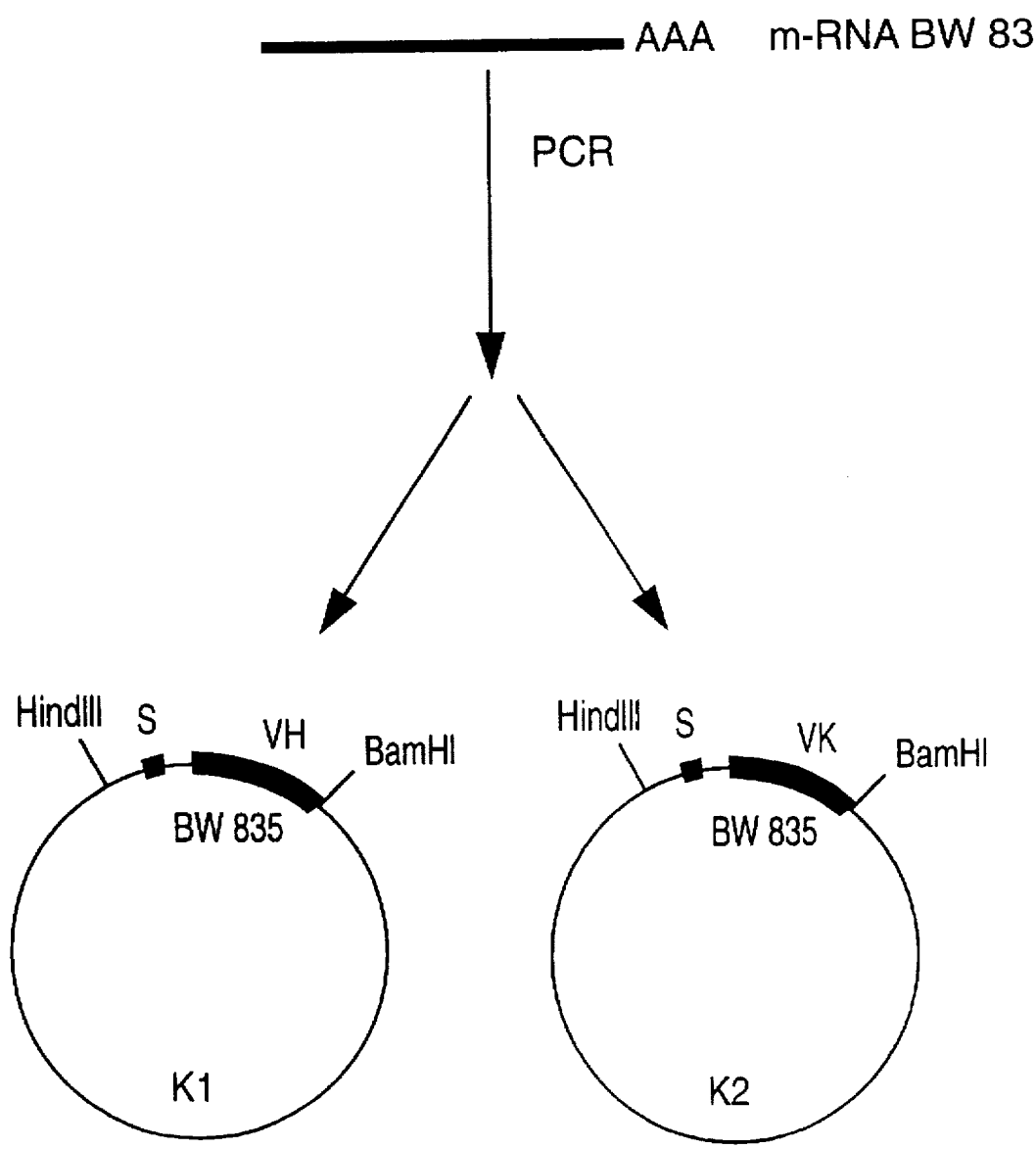
FIG. 12 shows the isolation of plasmids K1 and K2. See Example 10.

The $V_H$ and $V_K$ genes of the MAb BW 835 were amplified using the PCR technique and specific oligonucleotides by the method of Orlandi et al. (1989) and cloned in KS+ vectors (Güssow and Seemann (1991), Methods in Enzymology, Vol. 203) which contained $V_H$ and $V_K$ genes with suitable restriction cleavage sites (FIG. 11a for $V_H$ amd b for $V_K$). The clones K1 and K2 which contain the $V_H$ (K1) and $V_K$ (K2) genes of the MAb BW 835 were isolated (FIG. 12).

EXAMPLE 11

The nucleic acid sequences of the $V_H$ and $V_K$ genes of the MAb BW 835 from the clones K1 and K2 were determined by the method of Sanger et al. (1977) (FIGS. 1a, b) (SEQ ID NOS: 1-4). It is possible to generate mimetics based on the CDRs from this sequence by the method described by Saragovi et al. (Saragovi et al. (1991), Science 253, 792-795).

Figure 13:
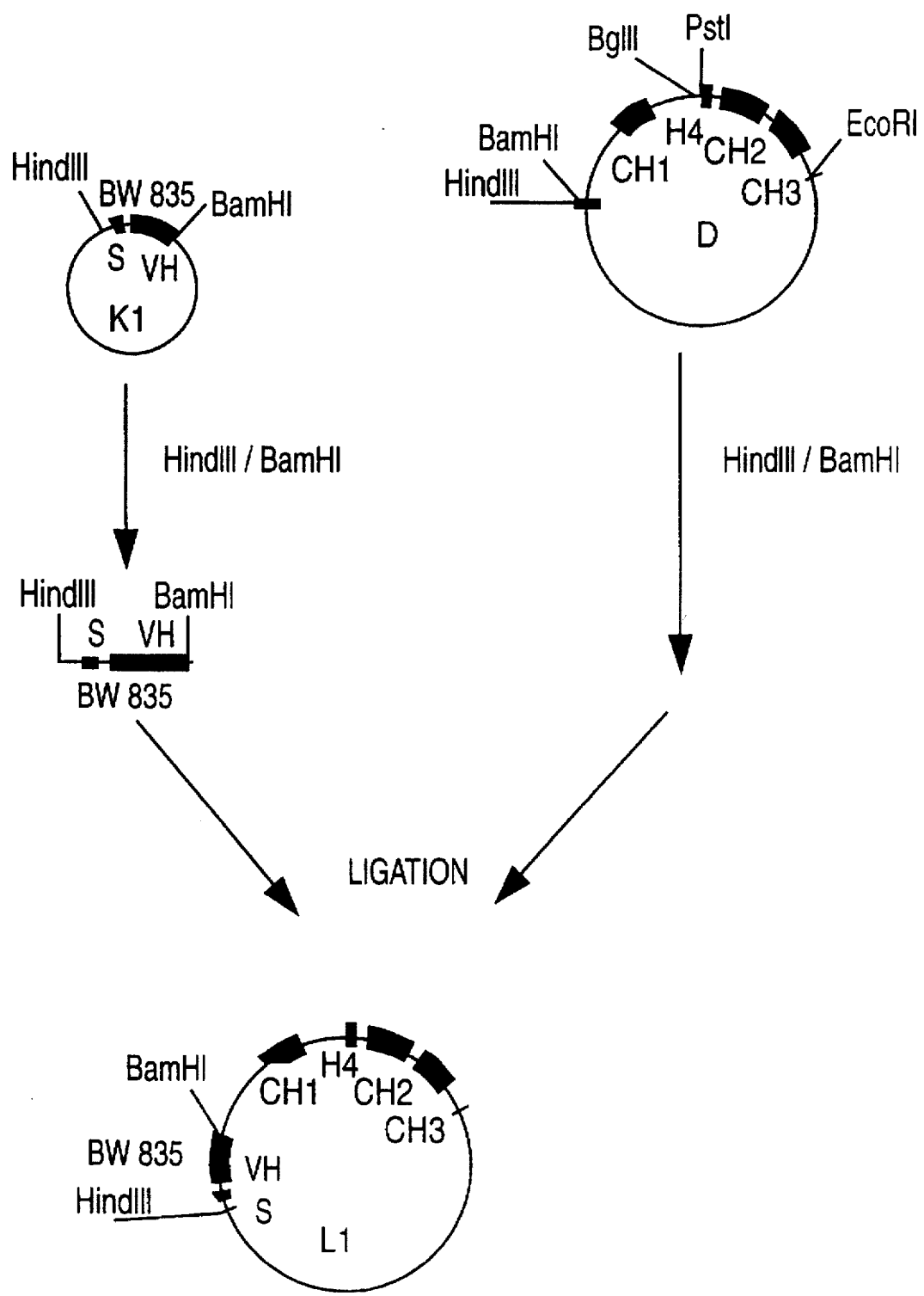
FIG. 13 shows the expression vector L1. See Example 11.
Figure 14:
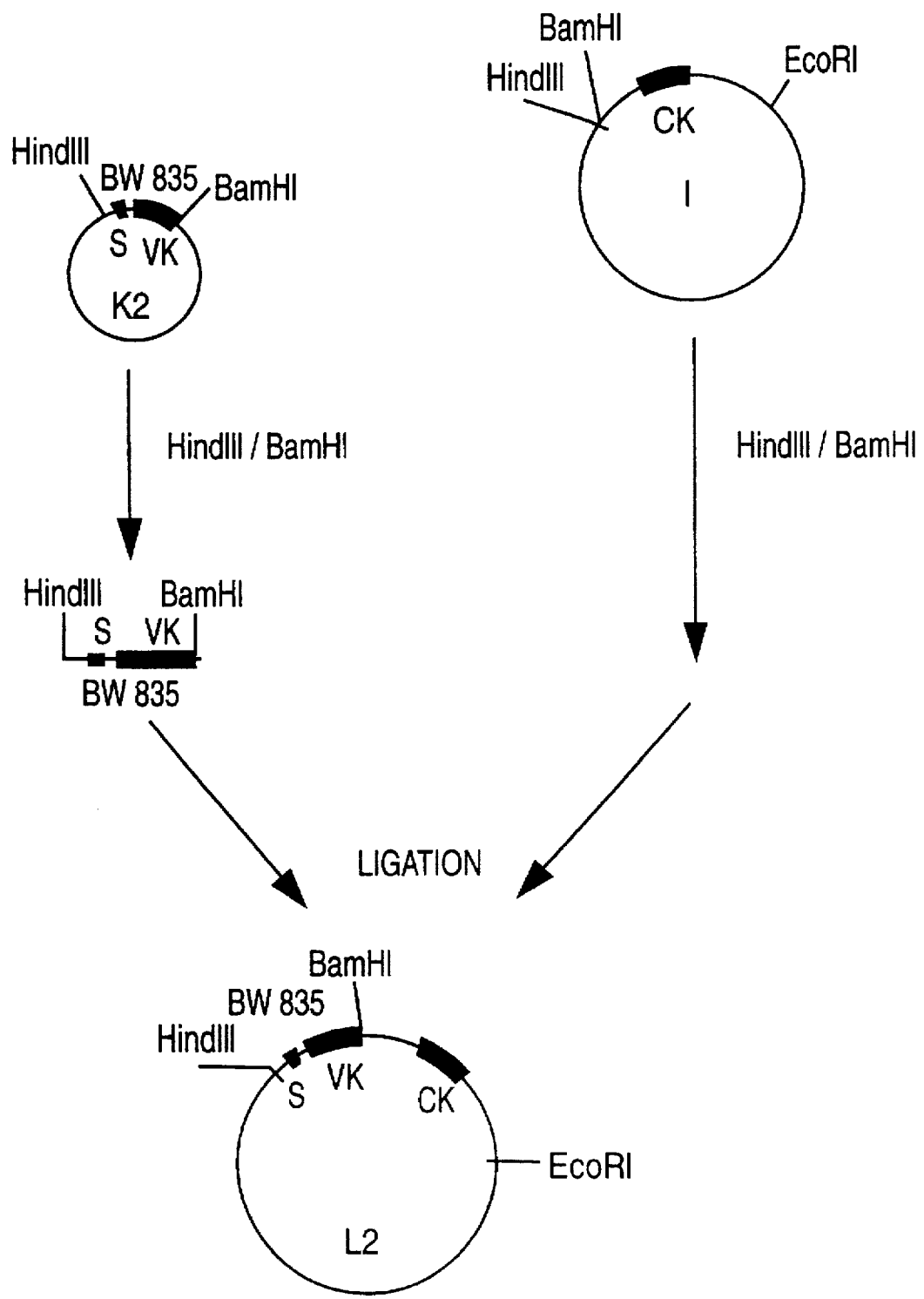
FIG. 14 shows the expression vector L2. See Example 11.

Furthermore, the $V_H$ and $V_K$ gene inserts were cut out of the clones K1 and K2 with the aid of the restriction endonucleases HindIII and BamHI and were cloned into the vectors D ($V_H$) and I ($V_K$) likewise cleaved with HindIII and BamHI. The expression vectors L1 and L2 which contain immunoglobulin heavy (L1) (FIG. 13) and light (L2) (FIG. 14) chain genes with the V genes of MAb BW 835 were isolated. The expression vectors L1 and L2 can be used for the expression of a chimeric MAb with the specificity of MAb BW 835.

Examples 12 and 13 are intended to explain the use of the MAb BW 835 for serodiagnosis of malignant tumors.

EXAMPLE 12

The MAb BW 835 was bound by adsorption to the walls of wells of microtiter plates (NUNC) by methods known to the person skilled in the art (Tijssen, P., "Practice and theory of enzyme immunoassay" Elsevier (1988), 297–328). 10 µl of sample were pipetted into each of the wells prepared in this way and each containing 100 µl of buffer (OSND, Behringwerke) and incubated at +37° C. for 2 hours. After washing three times with diluted Enzygnost washing buffer (OSEW, Behringwerke), 100 µl of MAb BW 835 (1 µg/ml) which was conjugated to peroxidase by known methods were introduced into each of the individual wells. The following 2-hour incubation step at +37° C. was completed by a cycle of three washes. Subsequently, for the third incubation step at room temperature, 100 µl of a buffer/substrate chromogen solution (OUVG/OUVF, Behringwerke) were pipetted into each of the wells, and the enzyme reaction was stopped after 30 minutes with 100 µl of Enzygnost stop solution (OSFA, Behringwerke). The extinction of the samples was determined as 450 nm.

Figure 15:
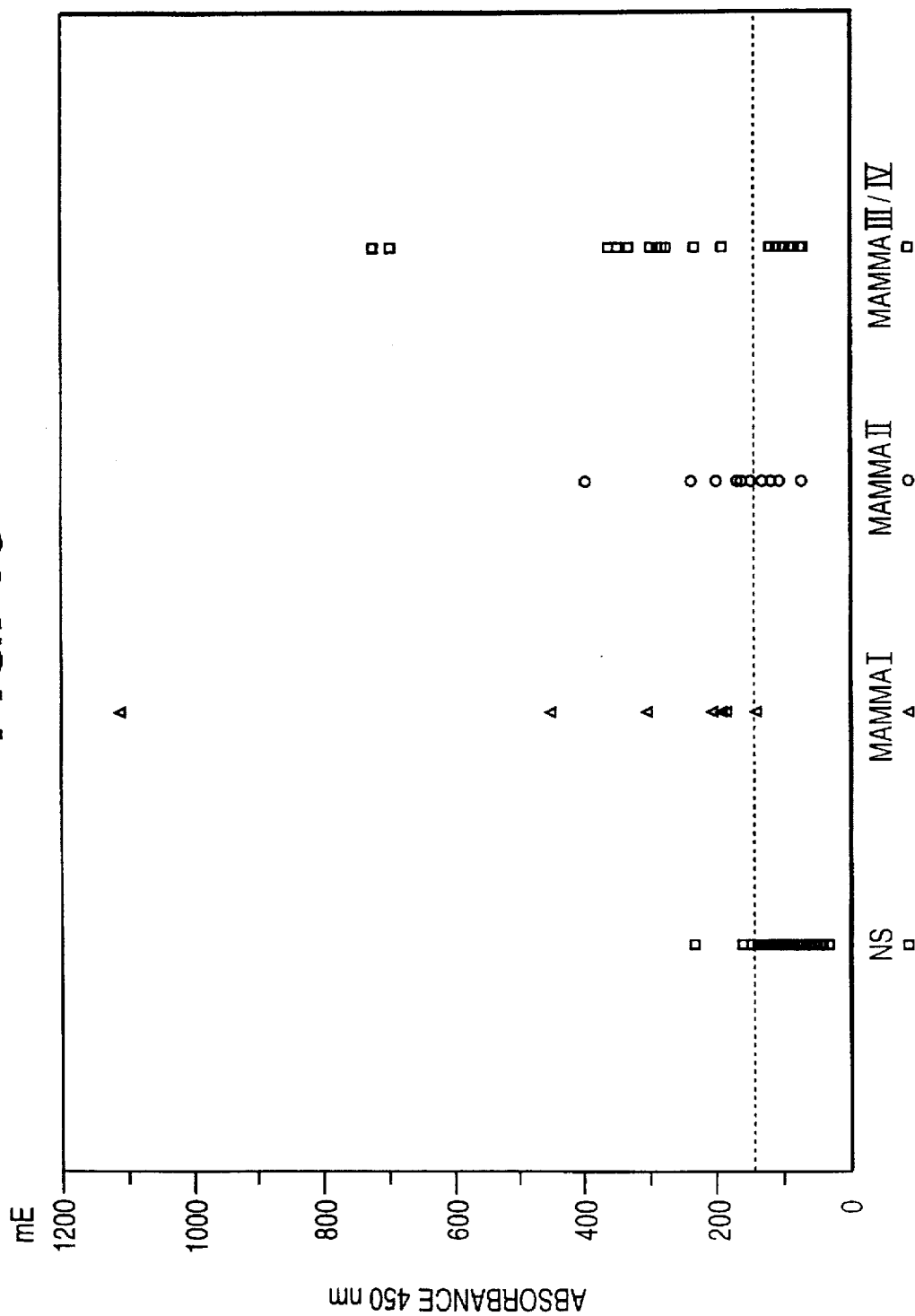
FIG. 15 compares the composition of concentration of antigen bound by MAb BW 835 in serum or plasma of patients with malignant tumors with that in healthy patients. See Example 12.

Result:

The extinctions determined in this way correspond in the level thereof to the concentration of the antigen in the sample. The concentration of the antigen defined by the specific binding of MAb BW 835 in serum or plasma of patients with malignant tumors is distinctly raised by comparison with that in healthy patients (FIG. 15). This particularly applies to patients with late-stage carcinoma of the breast, but also, surprisingly, to those with early-stage carcinoma who, with other commercial tumor marker tests for detecting breast cancer-associated antigens in serum (for example CA 15-3), by comparison give false-negative findings significantly more often, and thus overall better sensitivities were found for the homologous version described.

EXAMPLE 13

It is also possible to use for the detection of PEM in serum in the double-determinant assay in combination with the MAb BW 835 other peroxidase-labeled antibodies which recognize further epitopes on the tumor-associated antigens defined by MAb BW 835. To do this, for example, a test analogous to Example 12 was carried out using the DF3 antibody disclosed in the literature (Kufe et al. (1984), Hybridoma 3, 223) in peroxidase-labeled form (CA 15-3-Test, Boehringer Mannheim) as conjugate component.

Figure 16:
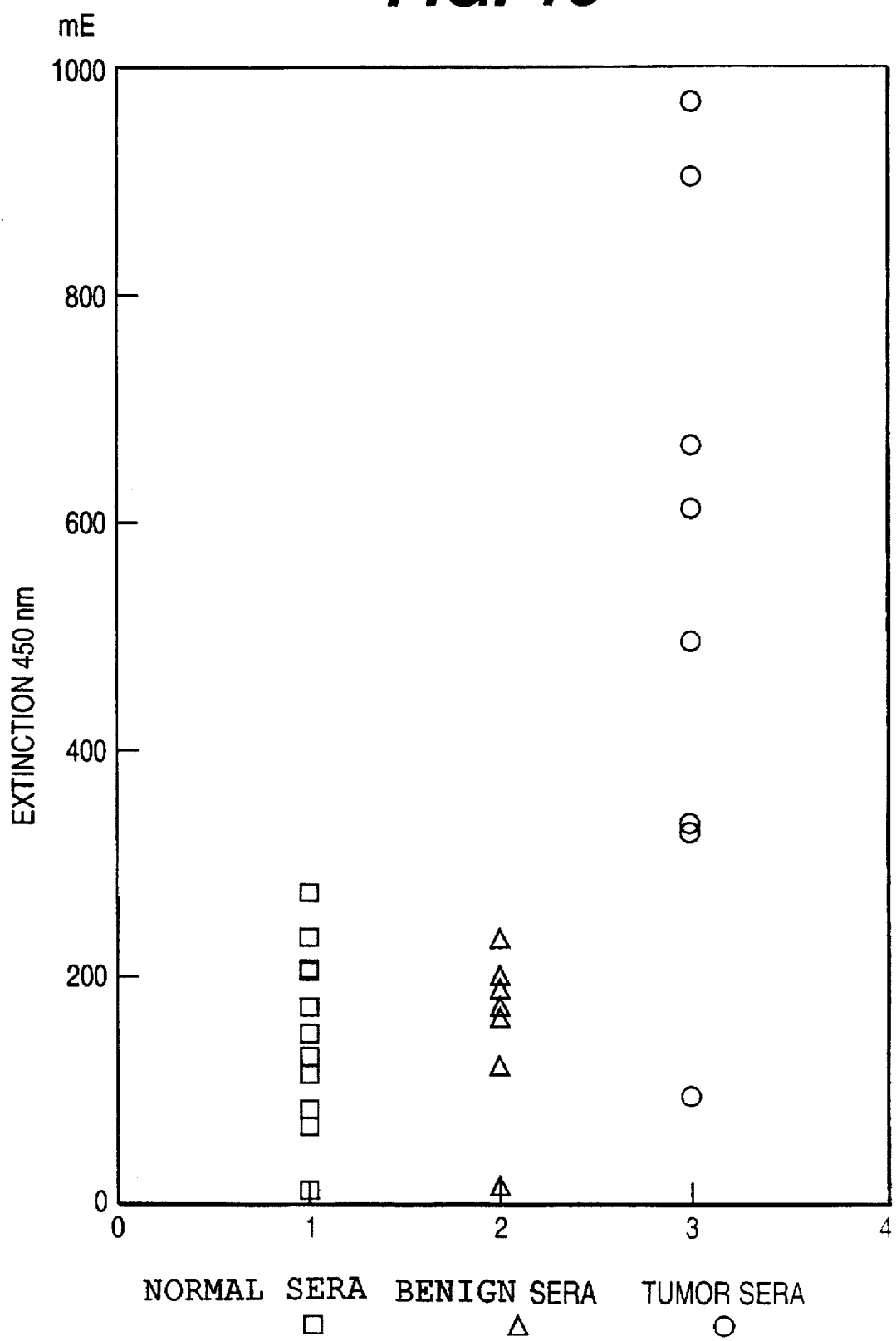
FIG. 16 compares the use of a peroxidase-labeled $DF_3$ antibody conjugate which recognizes further epitopes to the tumor-associated antigens defined by MAb BW 835 in tumor sera, normal sera and sera from patients with benign disease. See Example 13.

Result:

The use of, for example, DF3-POD as conjugate component to supplement the solid-phase-bound BW 835 produced distinctly higher serum values for the tumor sera compared with a normal serum pool and patients with benign diseases, which once again underlines the potential of the MAb BW 835 as specific component for a tumor marker test (FIG. 16).

---

We claim:

1. A monoclonal antibody, BW 835, which is produced by the hybridoma cell line DSM ACC2022, wherein the monoclonal antibody is immunoreactive with a polymorphic epithelial mucin (PEM) antigen associated with tumors selected from the group consisting of breast carcinomas, ovarian carcinomas, prostate carcinomas and lung adenocarcinomas.

2. A modified antibody that contains the CDR regions of the variable domains of BW 835 represented by SEQ ID No: 1 and SEQ ID No: 3, wherein the modified antibody is immunoreactive with a polymorphic epithelial mucin (PEM) antigen associated with tumors selected from the group consisting of breast carcinomas, ovarian carcinomas, prostate carcinomas and lung adenocarcinomas.

3. A modified antibody that comprises the CDR regions of the variable domains of BW 835 represented by SEQ ID No: 1 and SEQ ID No: 3, wherein the CDR regions are grafted onto a human framework and wherein the modified antibody is immunoreactive with a polymorphic epithelial mucin (PEM) antigen associated with tumors selected from the group consisting of breast carcinomas, ovarian carcinomas, prostate carcinomas and lung adenocarcinomas.

4. The antibody according to according to claim 3 wherein the framework region is modified in order to minimize the change in antigen binding properties of the antibody BW 835.

5. The hybridoma cell line DSM ACC2022 which produces the monoclonal antibody BW 835.

6. An antibody fragment of antibody BW 835 which binds to the same antigen as the monoclonal antibody of claim 1.

\* \* \* \* \*

UNITED STATES PATENT AND TRADEMARK OFFICE
CERTIFICATE OF CORRECTION

PATENT NO. : 5,695,758
DATED : December 09, 1997
INVENTOR(S) : Klaus BOSSLET et al.

It is certified that error appears in the above-indentified patent and that said Letters Patent is hereby corrected as shown below:

In claim 4, Column 12, line 37, delete "according to" (second occurrence).

Signed and Sealed this

Second Day of June, 1998

*Attest:*

BRUCE LEHMAN

*Attesting Officer*   *Commissioner of Patents and Trademarks*